United States Patent [19]

D'Orlando et al.

[11] Patent Number: 5,403,851
[45] Date of Patent: Apr. 4, 1995

[54] SUBSTITUTED TRYPTAMINES, PHENALKYLAMINES AND RELATED COMPOUNDS

[75] Inventors: Kay J. D'Orlando, Wayland; Kenneth W. Locke, Littleton; Emile M. Bellott, Beverly; Richard L. Gabriel, Swampscott; Michael D. Nohrden, Stow; Yesh P. Sachdeva, Concord; Salah A. Zahr, Acton; Emile Al-Farhan, West Roxbury; Subramaniam Krishnananthan, Waltham, all of Mass.

[73] Assignee: Interneuron Pharmaceuticals, Inc., Lexington, Mass.

[21] Appl. No.: 223,352

[22] Filed: Apr. 5, 1994

[51] Int. Cl.$^6$ ............... A61K 31/42; A61K 31/41; C07D 271/10; C07D 209/08
[52] U.S. Cl. .................. 514/364; 514/361; 514/381; 514/414; 514/415; 514/419; 548/125; 548/143; 548/144; 548/250; 548/252; 548/253; 548/254; 548/455; 548/457; 548/458; 548/465; 548/483; 548/492; 548/493; 548/494; 548/504; 548/506; 548/507
[58] Field of Search ............... 548/250, 252, 253, 254, 548/125, 455, 457, 458, 465, 483, 492, 493, 494, 504, 506, 507; 514/381, 361, 414, 415, 419

[56] References Cited

PUBLICATIONS

CA112:235837y Derivatives . . . antagonists Kerwin et al. p. 677, 1990.

Primary Examiner—Mary C. Lee
Assistant Examiner—Joseph K. McKane
Attorney, Agent, or Firm—Pennie & Edmonds

[57] ABSTRACT

This invention relates to novel substituted tryptamine and phenalkylamine and related compounds, pharmaceutical compositions thereof and methods of using said compounds and compositions for a number of pharmaceutical indications including (but not limited to): 1. central nervous system and psychiatric disorders (e.g., sleep disorders, epilepsy and other convulsive disorders, anxiety, psychiatric diseases, neurodegenerative diseases, fever); 2. chronobiological-based disorders (e.g., jet lag, delayed sleep syndrome, shift-work, seasonal affective disorder); 3. endocrine indications (e.g., contraception and infertility, precocious puberty, premenstrual syndrome, hyperprolactinemia, growth hormone deficiency); 4. cancer and other proliferative diseases; 5. immune system disorders and conditions associated with senescence; 6. ophthalmological diseases; 7. animal breeding (e.g., regulation of fertility, puberty, pelage color).

17 Claims, 6 Drawing Sheets

* Significantly Different from 0 Dose, $p<0.05$
Hexobarbital = 120 mg/kg, ip

* = Significantly Different from 0 Dose. p<0.05

SUBSTITUTED TRYPTAMINES, PHENALKYLAMINES AND RELATED COMPOUNDS

FIELD OF THE INVENTION

This invention relates to novel substituted tryptamine and phenalkylamine and related compounds, pharmaceutical compositions thereof, and methods of using said compounds and compositions for a number of pharmaceutical indications, including (but not limited to): 1. central nervous system and psychiatric disorders (e.g., sleep disorders, epilepsy and other convulsive disorders, anxiety, psychiatric diseases, neurodegenerative diseases, fever); 2. chronobiological-based disorders (e.g., jet lag, delayed sleep syndrome, shift-work, seasonal affective disorder); 3. endocrine indications (e.g., contraception and infertility, precocious puberty, premenstrual syndrome, hyperprolactinemia, growth hormone deficiency); 4. cancer and other proliferative diseases; 5. immune system disorders and conditions associated with senescence; 6. ophthalmological diseases; and 7. animal breeding (e.g., regulation of fertility, puberty, pelage color).

BACKGROUND OF THE INVENTION

The novel compounds described herein are structurally related to the known naturally occurring substance, melatonin. Melatonin, 5-methoxy-N-acetyltryptamine, is a hormone produced primarily by the pineal gland. The synthesis and secretion of melatonin exhibit a circadian rhythm that changes with the seasons and with age, e.g., pubescence and senescence. The rhythm is the result of both endogenous mechanisms and environmental cues, most notably, the exposure of organisms to light, which inhibits melatonin synthesis and secretion. Thus, melatonin levels are high at night and low during the day. There is very strong evidence that melatonin is important for the regulation of a variety of neural and endocrine functions, especially those that exhibit circadian and circannual rhythmicity.

Novel compounds related to melatonin, but with pharmacological or pharmacokinetic profiles different from melatonin, are likely to be important new pharmaceuticals. For examples, see U.S. Pat. Nos. 5,151,446 of Horn et al., 5,194,614 of Adrieux et al. and 5,276,051 of Lesieur et al. There is evidence suggesting both melatonin agonists and antagonists would be of potential therapeutic use.

Melatonin has been implicated in many human disorders. Some disorders are known to be linked to chronobiologic abnormalities. Melatonin has been administered to re-synchronize circadian rhythms that are out of phase with the local environmental cues; i.e. chronobiological therapy. For example, sleep/wake disorders associated with rapid crossing of time zones (jet lag), changes in work shifts, or those experienced by blind people can be treated with melatonin or melatonin analogs (see U.S. Pat. Nos. 4,600,723 and 4,665,086 of Short et al., and 5,242,941 of Lewy et al.).

However, it appears that melatonin also has direct sedative/hypnotic properties in normal human subjects. Several groups of investigators have demonstrated sleepiness following intravenous, oral and intranasal administration of melatonin to humans (e.g. Waldhauser et al., *Psychopharmacology*, 100: 222–226, 1990; Vollrath et al., *Bioscience* 29:327–329, 1981; Dollins et al., *Proc. Natl. Acad. Sci.*, 99:1824–1828, 1994). It appears that melatonin does not have the side-effect liability associated with current hypnotics, e.g. amnesia, "hangover", dependence and tolerance.

Sedative/hypnotic agents often exhibit other useful properties, such as anxiolytic and antiseizure actions. Melatonin has been demonstrated in a number of rodent experimental paradigms to have both anxiolytic (Golus and King, *Pharmacol. Biochem. Behav.* 15:883–885, 1981; Guardiola et al., *Pharmacol. Biochem Behav.* 41:405–408, 1992, Naranjo-Rodriguez et al., *Soc. Neurosci. Abst.* 18:1167, 1992; Golombek et al., *Eur. J. Pharmacol.* 237:231–236, 1993) and antiseizure activity (Brailowsky, *Electroencephalo. Clin. Neurophysiol.* 41:314–319, 1976; Fariello et al., *Neurology* 27:567–570, 1977, Rudeen et al., *Epilepsia* 21:149–154, 1980; Sugden, *J. Pharmacol. Exp. Ther.* 227:587–591, 1983; Golombek et al., *Eur. J. Pharmacol.* 210:253–258, 1992). In humans with panic disorder, a severe anxiety problem, melatonin secretion is abnormal (Mcintyre et al., *Am. J. Psychiat.* 147:462–464, 1990).

Melatonin may play a role in other psychiatric conditions, particularly depression, but also mania and schizophrenia (see Dubocovich "Antidepressant Agents", U.S. Pat. No. 5,093,352; Miles and Philbrick, *Biol. Psychiatry* 23:405–425, 1988; Sandyk and Kay, *Schizophr. Bull.* 16:653–662, 1990). In some instances, psychiatric disorders may have underlying chronobiologic etiologies (e.g. seasonal affective disorder) and are definite candidates for melatonin therapy.

Melatonin is involved in the regulation of circadian and circannual changes in body temperature. Administration of exogenous melatonin to humans lowers core body temperature (Strassman et al., *J. Appl. Physiol.* 71:2178–2182, 1991; Cagnacci et al., *J. Clin. Endocrinol. Metab.* 75:447–452, 1992). Melatonin may also possess analgesic properties (Sugden, *J. Pharmacol. Exp. Ther.* 227:587–591, 1983). Therefore, melatonin-like compounds may be useful as an alternative to non-steroidal anti-inflammatory, anti-pyretic drugs, such as aspirin, acetaminophen and ibuprofen.

It is known that melatonin levels decrease with advancing age (Sack et al., *J. Pineal Res.* 4:379–388, 1986; Waldhauser et al., *J. Clin. Endocrinol. Metab.* 66:648–652, 1988; Van Coevorden et al., *Am. J. Physiol.* 260:E651–661, 1991) which may contribute to some disorders. Neurodegenerative diseases often associated with aging, such as Alzheimer's and Parkinson's diseases, may be treated with melatonergic compounds (Maurizi, *Med. Hypotheses* 31:233–242, 1990; Sandyk, *Int. J. Neurosci.* 50:37–53, 1990; Skene et al., *Brain Res.* 528:170–174, 1990). Sleep disorders in the elderly recently have been shown to respond to melatonin treatment (Haimov and Lavie, unpublished findings). Even osteoporosis may have a melatoninergic component (Sandyk et al., *Int. J. Neurosci.* 62:215–225, 1992). In fact, melatonin has been suggested to be an anti-aging, anti-stress hormone (Armstrong and Redman, *Med. Hypotheses* 34:300–309, 1991; Reiter, *Bioessays* 14:169–175, 1992). This may be due to its action as a free radical scavenger (Poeggeler et al., *J. Pineal Res.* 14:151–168, 1993) or its interaction with the immune system (Maestroni and Conti, *J. Neuroimmun.* 28:167–176, 1990; Fraschini et al., *Acta. Oncol.* 29:775–776 1990; Guerrero and Reiter, *Endocr. Res.* 18:91–113, 1992).

Related to the above, are the findings that melatonin has oncostatic properties in a variety of cancers, the most studied being its effects on estrogen receptor positive breast cancers (Blask and Hill, *J. Neural Transm. Suppl.* 21:433–449, 1986; Gonzalez et al. *Melanoma Res.* 1:237–243, 1991; Lisoni et al., *Eur. J. Cancer* 29A:1-85-189, 1993; Shellard et al., *Br. J. Cancer* 60:288–290, 1989; Philo and Berkowitz, *J. Urol.* 139:1099–1102, 1988; see U.S. Pat. Nos. 5,196,435 of Clemens et al. and 5,272,141 of Fraschini et al.). It is also possible that melatonin has antiproliferative effects on noncancerous cells as well, and may be of use to treat benign tumors and proliferative diseases such as psoriasis.

A major portion of research on melatonin has been devoted to studying its effects on reproduction, particularly in seasonally-breeding species (such as hamsters and sheep), in which melatonin is known to regulate fertility and puberty, hibernation, and coat color. These effects have obvious significance for animal husbandry use. Reproductive endocrine uses in humans for melatonin include: contraceptive and fertility agents, treatment for precocious puberty, treatment for premenstrual syndrome and hyperprolactinemia (Fevre et al., *J. Clin. Endocrinol. Metab.* 47:1383–1386, 1978; Parry et al., *Am. J. Psychiatry* 144:762–766, 1987; Waldhauser et al., *J. Clin. Endocrinol. Metab.* 73:793–796, 1991; Bispink et al., *J. Pineal Res.* 8:97–106, 1990; Cagnacci et al., *J. Clin. Endocrinol. Metab.* 73:210–220, 1991; Voordouw et al., *J. Clin. Endocrinol. Metab.* 74:107–108, 1992; see U.S. Pat. Nos. 4,855,305 and 4,945,103 of Cohen et al., and 5,272,141 of Fraschini et al.) It is likely that melatonin compounds may also be useful in other endocrine conditions, particularly those involving growth hormone (Cramer et al., *Arzneim.-Forsch.* 26:1076–1078, 1976; Wright et al., *Clin. Endocrinol.* 24:375–382, 1986; Paccotti et al., *Chronobiologica* 15:279–288, 1988; Valcavi et al., *Clin. Endocrinol.* 39:193–199, 1993).

In addition to the pineal gland, the eye also synthesizes melatonin. Recently melatonin has been implicated in the control of intraocular pressure and may be of use in glaucoma (Samples et al., *Curr. Eye Res.* 7:649–653, 1988; Rhode et al., *Ophthalmic Res.* 25:10–15, 1993). Research on the function of melatonin in the eye may uncover additional novel therapeutic uses.

It is clear that there exists a broad range of therapeutic uses for melatonin. Accordingly, it is of continuing interest to identify novel compounds that interact with melatonergic systems as potential therapeutic agents. These compounds may offer improved pharmacokinetic (i.e. longer duration, greater potency) and/or pharmacodynamic (i.e. greater efficacy) actions to those of melatonin. This invention addresses the need for more therapeutically effective compounds than melatonin.

Citation or identification of any reference in this section of this application shall not be construed as an admission that such reference is available as prior art to the present invention.

SUMMARY OF THE INVENTION

One embodiment of the present invention is directed to compounds having the following structure:

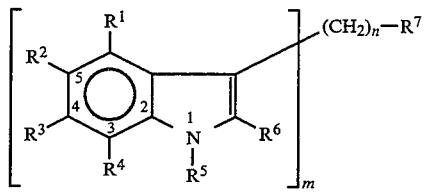

wherein:
$R^1$, $R^2$, $R^3$ and $R^4$ are independently hydrogen, halogen, hydroxy, alkoxy or alkyaryl;
$R^5$ is hydrogen, alkyl, alkylaryl or acetyl;
$R^5$ is hydrogen, alkyl, alkylaryl or halogen;
n is 0 to 2;
m is 1 to 2;
$R^7$ is

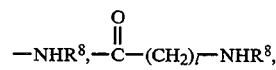

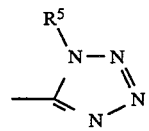

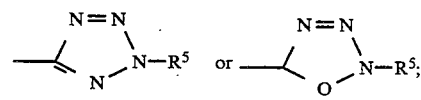

l is 0 to 2;
$R^8$ is hydrogen,

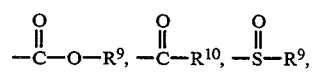

or $R^9$;
$R^9$ is alkylene, aryl, alkylaryl, alkylcycloalkyl,

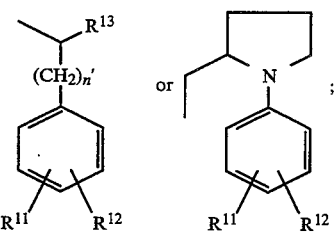

$R^{10}$ is cycloalkyl, $CF_3$, $CH_3$,

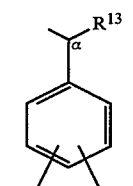

or

-continued

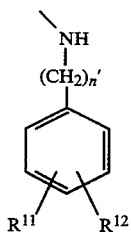

the carbon site at position α is a chiral center, and may be S or R;
$R^{11}$ and $R^{12}$ are hydrogen;
$R^6$ and $R^7$ are optionally connected together to form a cyclic group; and
$R^{13}$ is alkyoxy, hydroxy, hydrogen, thioalkyl, alkylcycloalkyl or

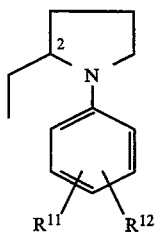

n' is 0 to 2; the carbon site at position 2 of the pyrrole ring is a chiral center, and may be S or R.
with the proviso that if $R^6$ is hydrogen, $R^7$ is —$NHR^8$ and
$R^8$ is

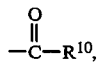

then $R^{13}$ is not hydrogen; if n is 2, then $R^{10}$ is not cycloalkyl $CF_3$ or

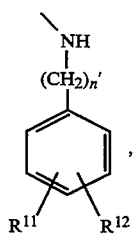

where n' is 1 to 2; if m is 1, $R^9$ is not alkylene; optionally, $R^6$ and $R^7$ are connected together to form a cyclic group, so as to form, for example, the following structure:

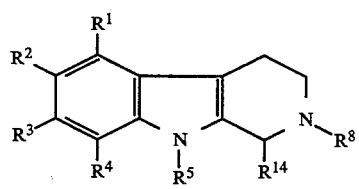

where $R^8$ is hydrogen or

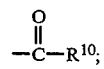

and
$R^{14}$ is hydrogen, alkyl, halogen, alkoxy, aryl or aklylaryl.

Another embodiment of the present invention is directed to compounds having the following structure:

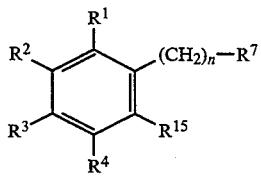

wherein:
$R^1$, $R^2$, $R^3$ and $R^4$ are independently hydrogen, halogen, hydroxy, alkoxy or alkyaryl;
n is 0 to 2;
$R^7$ is

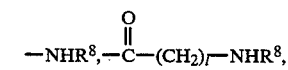

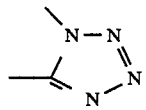

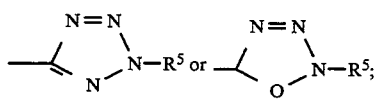

l is 0 to 2;
$R^8$ is hydrogen,

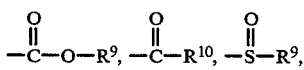

or $R^9$;
$R^9$ is alkylene, aryl, alkylaryl, alkylcycloalkyl,

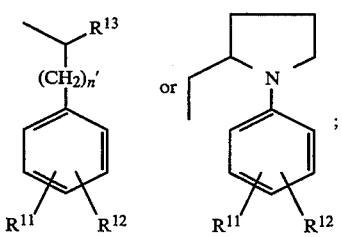

$R^{10}$ is cycloalkyl, $CF_3$, $CH_3$,

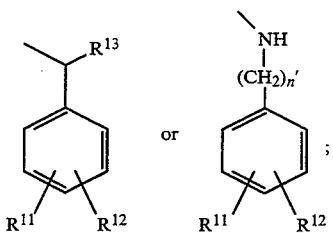 or 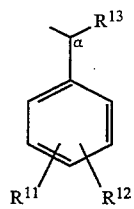 ;

n' is 0 to 2;
R$^{11}$ and R$^{12}$ are hydrogen; and
R$^{15}$ is hydrogen, halogen, hydroxy, alkoxy or alkylaryl,
Preferred compounds of the present invention are those of the formula:

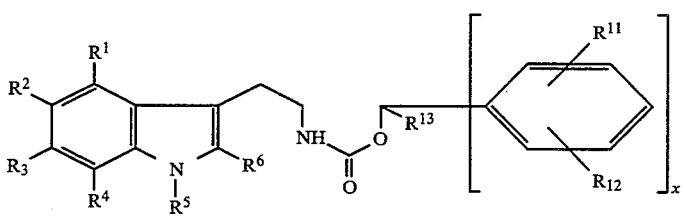

wherein:
R$^1$, R$^2$, R$^3$ and R$^4$ are independently hydrogen, halogen hydroxy or alkoxy;
R$^5$ is hydrogen;
R$^6$ is hydrogen or halogen;
x is 0 or 1;
R$^{11}$ and R$^{12}$ are independently hydrogen, —NO$_2$, alkoxy, CF$_3$, alkyl, halogen or R$^{11}$ taken together with R$^{12}$ is

 ;

and
R$^{13}$ is hydrogen, thioalkyl, alkylcycloalkyl or

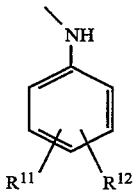

with the proviso that if R$^6$ is hydrogen, R$^{13}$ is not hydrogen.
Further preferred compounds of the present invention are those of the formula

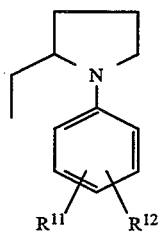

wherein R$^1$, R$^2$, R$^3$ and R$^4$ are independently hydrogen or alkoxy;
R$^5$ is hydrogen;
R$^6$ is hydrogen;
R$^{10}$ is

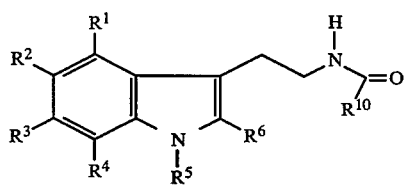

or

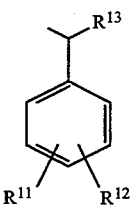

R$^{11}$ and R$^{12}$ are hydrogen; and
R$^{13}$ is alkyoxy or hydroxy; the carbon site at position α is a chiral center, and may be S or R.
Still further preferred compounds of the present invention are those of the formula

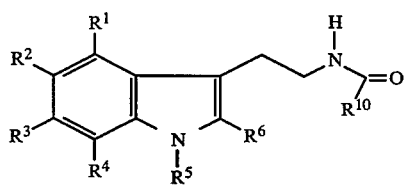

wherein R$^1$, R$^2$, R$^3$ and R$^4$ are independently hydrogen or halogen,
and R$^{10}$ is alkoxycycloalkyl,

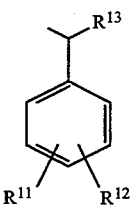

-continued

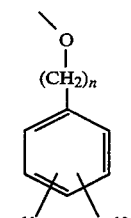

or

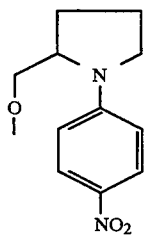

n is 0 or 1

$R^{11}$ and $R^{12}$ are independently hydrogen, halogen, alkyl, $CF_3$, $NO_2$ or $R^{11}$ taken together with $R^{12}$ is

and, $R^{13}$ is hydrogen; and $R^{15}$ is hydrogen.

Specifically preferred are the following compounds:
N-(p-Methoxybenzyloxycarbonyl)tryptamine;
N-(Benzyloxycarbonyl)-5-methoxytryptamine;
N-(p-methoxybenzyloxycarbonyl)-5-methoxytryptamine;
6-methoxy-1-methyl-1,2,3,4-tetrahydro-β-carboline;
1-phenyl-1,2,3,4-tetrahydro-β-carboline;
2-acetyl-1,2,3,4-tetrahydro-β-carboline;
N-(Benzyloxycarbonyl)-2-phenylethylamine;
N-(Benzyloxycarbonyl)-5-hydroxytryptamine;
N-(Benzyloxycarbonyl)-5-fluorotryptamine;
N-(2-phenylethyl)-phenylacetamide;
3-(5-tetrazolyl)indole;
1-benzyl-3-(1-benzyl-5-tetrazolyl)indole;
1-benzyl-3-(2-benzyl-5-tetrazolyl)indole;
1-benzyl-3-(5-tetrazolyl)indole;
1-benzyl-3-[5-2-methyl-1,3,4-oxadiazolyl)indole;
N-(Benzyloxycarbonyl)-6-fluorotryptamine;
N-(p-methoxybenzyloxycarbonyl)-5-fluorotryptamine;
N-(4-Fluorobenzyloxycarbonyl)-5-fluorotryptamine;
1-acetyl-3-[5-2-methyl-1,3,4 oxadiazolyl)indole;
6-Benzyloxy-1-phenyl-1,2,3,4-carboline;
N-(Benzyloxycarbonyl)-5-chlorotryptamine;
N-(2-p-Fluorophenylethyl)phenylacetamide;
N-(2-m-Fluorophenylethyl)phenylacetamide;
N-(Benzyloxycarbonyl)-2-(m-fluorophenyl)ethylamine;
N-Benzyloxycarbonyl-2-(p-fluorophenyl)ethylamine;
N-(p-Fluorobenzyloxycarbonyl)-2-(m-fluorophenyl)ethylamine;
N-(p-Fluorobenzyloxycarbonyl)-2-(p-fluorophenyl)ethylamine;
N-(p-Trifluoromethylbenzyloxycarbonyl)-2-(p-fluorophenyl)ethylamine;
N-(p-Trifluoromethylbenzyloxycarbonyl)-2-m-fluorophenyl)ethylamine;
N-(p-Chlorobenzyloxycarbonyl)tryptamine;
N-(p-Methylbenzyloxycarbonyl)tryptamine;
N-(p-Chlorobenzyloxycarbonyl)-2-(p-fluorophenyl)ethylamine;
N-(p-Methylbenzyloxycarbonyl)-2-(p-fluorophenyl)ethylamine;
N-(3,4-Dimethylbenzyloxycarbonyl)-2-(p-fluorophenyl)ethylamine;
N-(p-Isopropylbenzyloxycarbonyl)tryptamine;
N-(3,4-Dimethylbenzyloxycarbonyl)tryptamine;
N-(p-Trifluoromethylbenzyloxycarbonyl)tryptamine;
N-(p-Nitrobenzyloxycarbonyl)-5-fluorotryptamine;
N-(3,4-methylenedioxybenzyloxycarbonyl)tryptamine;
N-(3,4-Methylenedioxybenzyloxycarbonyl)-2-(p-fluorophenyl)ethylamine;
N-[(S)-α-Methylbenzyloxycarbonyl]tryptamine;
N-(p-Isopropylbenzyloxycarbonyl)-2-(p-fluorophenyl)ethylamine;
N-Cyclopropanemethyloxycarbonyl)-5-methoxytryptamine;
N[(R)-α-methylbenzyloxycarbonyl]-tryptamine;
2-Bromo-N-(Benzyloxycarbonyl)tryptamine;
N-[(S)-(−)-1,4(nitrophenyl)-2-pyrrolidinemethyloxycarbonyl]tryptamine;
p-Fluorophenyl-N-[(S)-(−)-1,4(nitrophenyl)-2-pyrrolidinemethyloxycarbonyl]ethylamine;
N-(Cyclohexylmethyloxycarbonyl)-4-fluorophenylethylamine;
N-Cyclopentylmethyloxycarbonyl-5-fluorotryptamine;
N-Cyclobutylmethyloxycarbonyl-5-fluorotryptamine;
2-formamido-5-methoxy-β-acetamidopropiophenone;
N-(Benzenesulfonyl)tryptamine;
N-(1-(R)-Methoxy-1-phenylacetyl)tryptamine;
N-(1-(S)-Methoxy-1-phenylacetyl)tryptamine;
N-Cyclopropylmethyloxycarbonyltryptamine;
2-Bromo-N-cyclopropylmethyloxycarbonyltryptamine;
2-Bromo-5-fluoro-N-benzyloxycarbonyltryptamine;
N-[2-(m-fluoro)phenylethyl]-p-trifluoro-methylphenyl acetamide;
2-benzyltryptamine;
N-[(S)-mandeloyl]tryptamine;
N-[(R)-mandeloyl]tryptamine;
N-(m-Fluorophenylethyl)-4-fluorophenylacetamide;
N-(p-fluorophenylethyl)-4-fluorophenylacetamide;
2-benzyl-5-methoxytryptamine;
1-[5-Fluoro-3-(2'-ethyl)indolyl]-3-benzylurea;
Di-[N-(methyleneoxycarbonyl)-tryptamine]-1,4-ciscyclohexane; and
di-[N-(methyleneoxycarbonyl)-tryptamine]-N-octane.

Another embodiment of the invention is directed to compositions comprising a compound of formulas I or II for indications including (but not limited to): 1. chronobiological-based disorders (e.g., jet lag, delayed sleep syndrome, shift-work, seasonal affective disorder); 2. central nervous system and psychiatric disorders (e.g., sleep disorders, epilepsy and other convulsive disorders, anxiety, psychiatric diseases, neurodegenerative diseases, fever); 3. endocrine indications (e.g., contraception and infertility, precocious puberty, premenstrual syndrome, hyperprolactinemia, growth hormone deficiency); 4. cancer and other proliferative diseases; 5. immune system disorders and conditions associated with senescence; 6. ophthalmological diseases; and 7. animal breeding (e.g., regulation of fertility, puberty, pelage color).

Another embodiment of the present invention is directed to a method of treating the above described indications by administering a therapeutically effective amount of one or more of the novel compounds of formulas I or II to a subject suffering from such indication and also for enhancing the actions of other hypnotics, sedatives or anxiolytics.

Preferred is the method of inducing sedation with a therapeutically effective amount of one or more of the compounds of the present invention to a subject requiring sedation, or who may benefit from sedation (e.g., prior to surgery or invasive medical procedures, or one who is suffering from stress).

Another preferred embodiment of the present invention comprises a method of treating various sleep disorders by administering a therapeutically effective amount of one or more of the compounds of the present invention to a subject suffering from one or more of such disorders, including insomnia.

Another preferred embodiment of the present invention comprises a method of treating disorders of chronobiology, such as sleep cycle disturbances and anxiety resulting therefrom, including jet lag, workshift changes and time zone changes.

Another preferred embodiment of the present invention comprises a method of treating various psychological or psychiatric conditions relating to anxiety or depression.

DESCRIPTION OF THE INVENTION

Figure 1:
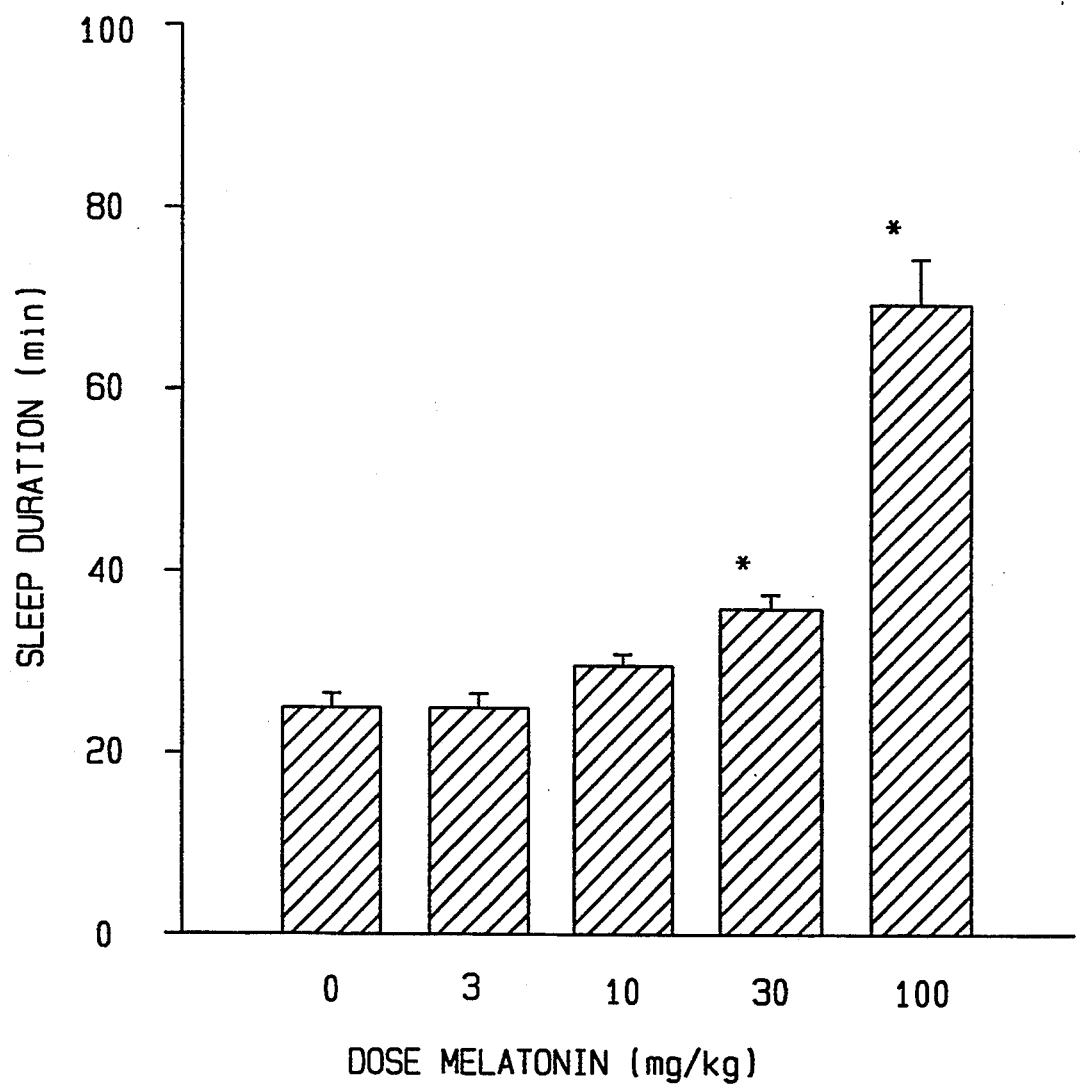
FIG. 1 is a bar graph showing the effect of various intraperitoneal dosages of melatonin on the duration of hexobarbital-induced sleep in mice.

As used herein and in the claims, the term "alkyl" means straight or branched hydrocarbon chain having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl.

As used herein and in the claims, the term "alkoxy" means straight or branched chain alkyl attached by an oxygen molecule, having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy.

As used herein and in the claims, the term "alkylcycloalkyl" means a $C_3$ to $C_{10}$ saturated hydrocarbon ring with an alkylene substituent of $C_1$ to $C_6$ linear or branched carbon atoms and includes methylenecyclopropyl, methylenecyclobutyl, methylenecyclopentyl, etc. The term "alkylene, refers to linear or branched chain alkylene groups having 1 to 10 carbon atoms and includes for example, the groups methylene, dimethylmethylene, ethylene 2,2-dimethylpropylene, 2-dimethylbutylene and the like and includes benzyl, 2-phenylethylene, 3-phenyl-2,2-dimethylpropylene, etc.

As used herein and in the claims, the term "halogen" means fluorine, chlorine, bromine and iodine.

As used herein and in the claims, the phrase "therapeutically effective amount" means that amount of novel compounds or compositions of the present invention necessary to administer to a host to achieve the desired results for the indications including (but not limited to): 1. chronobiological-based disorders (e.g., jet lag, delayed sleep syndrome, shift-work, seasonal affective disorder); 2. central nervous system and psychiatric disorders (e.g., sleep disorders, epilepsy and other convulsive disorders, anxiety, psychiatric diseases, neurodegenerative diseases, fever); 3. endocrine indications (e.g., contraception and infertility, precocious puberty, premenstrual syndrome, hyperprolactinemia, growth hormone deficiency); 4. cancer and other proliferative diseases; 5. immune system disorders and conditions associated with senescence; 6. ophthalmological diseases; 7. animal breeding (e.g., regulation of fertility, puberty, pelage color), or to achieve the desired enhanced actions of other known pharmaceutical compositions, such as hypnotics, sedatives or antidepressants.

SYNTHESIS

The compounds of formulas I and II provided by the present invention can be prepared by methods generally known to those skilled in the art or by novel methods described herein.

Pharmaceutically suitable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

Preparation of the novel compounds of the invention will be illustrated by the following nonlimitative specific examples.

N-(p-Methoxybenzyloxycarbonyl)tryptamine

To a suspension of 0.70 g (4.7 mmol) of tryptamine in 2.5 mL of deionized water and 0.65 mL (4.7 mmol) of triethylamine in a round bottom flask, equipped with an argon inlet, was added 1.45 g (4.7 mmol) of 2-(4-methoxybenzyloxycarbonyloxyimino)-2-phenylacetonitrile (Moz-ON, Aldrich) in 5 mL of dioxane. During the first 5-10 minutes of stirring, the mixture became clear. This mixture was stirred for an additional 6 hours and diluted with 150 mL of saturated sodium chloride solution and extracted with 2×50 mL of ethyl acetate. The organic extracts were dried over anhydrous sodium sulfate and concentrated in vacuo. The residue was purified by flash chromatography using hexane:ethyl acetate (1:1) as an eluent to yield (81%) N-(p-Methoxybenzyloxycarbonyl)tryptamine as white solid, mp. 108°–109° C.

$^1$H NMR (CDCl$_3$) δ7.7–6.8 (m, 9H), 5.1(s, 2H), 3.8(s,3H), 3.5(q,2H), 2.9(t, 2H).

IR (KBr) 3400–3260, 1620, 1510, 1420, 1230 Cm$^{-1}$. Analysis calculated for C$_{19}$H$_{20}$N$_2$O$_3$: C, 70.35; H, 6.21; N, 8.63 Found: C, 70.45; H, 6.36; N, 8.61.

N-(p-Methoxybenzyloxycarbonyl)tryptamine hydrochloride

To a solution of 2 g of N-(p-methoxybenzyloxycarbonyl)tryptamine in 100 mL of ethyl acetate, 20 mL of saturated ethereal solution of HCl gas was added. The solvent was evaporated and the residue was dried in a vacuum desicator which resulted in 2.08 g of N-(p-methoxybenzyloxycarbonyl)tryptamine hydrochloride as a tan solid.

$^1$H NMR (Acetone-d$_6$) δ7.8–6.9 (m, 9H), 5.1 (s, 2H), 3.8 (s, 3H), 3.5 (q, 2H), 3.0 (t, 2H).

IR (KBr) 3400, 3310, 2900, 1690, 1600, 1540, 1510, 1450, 1250 Cm$^{-1}$.

N-(Benzyloxycarbonyl)-5-fluorotryptamine

To a strirred solution of 0.83 g (4–6 mmol) of 5-fluorotryptamine and 0.48 g (0.55 mL, 5 mmol) of nmethylmorpholine in 10 mL of DMF at 0° C. was added dropwise 0.72 mL (5 mmol) of benzylchloroformate. The reaction mixture was allowed to stir at 0° C. under argon. After 1.5 hours of stirring, the reaction mixture was diluted with water and extracted with ethyl acetate. The organic extracts were washed with saturated sodium chloride, dried over anhydrous Na$_2$SO$_4$, and concentrated under vacuum. The resulting residue was purified by flash chromatography using hexane:ethyl acetate (2:1) as an eluent to yield 1 g (68%) of N-(Benzyloxycarbonyl)-5-fluorotryptamine as a white solid. mp 104°–105° C.

$^1$H NMR (CDCl$_3$) δ7.4 (s, 5H), 7.39–6.85 (m, 4H), 5.15 (s, 2H), 3.5 (q, 2H), 2.9 (t, 2H).

IR (KBr) 3500–3100, 1690, 1510, 1480, 1450, 1250 Cm$^{-1}$. Analysis calculated for C$_{18}$H$_{17}$FN$_2$O$_2$: C, 69.22; H, 5.49; N, 8.99; F, 6.08 Found: C, 69.19; H, 5.57; N, 8.95; F, 6.21.

N-(Benzyloxycarbonyl)-6-fluorotryptamine

To a strirred solution of 2.0 g (11.2 mmol) of 6-fluorotryptamine and 1.2 mL (11.2 mmol) of nmethylmorpholine in 20 mL of DMF at 0° C. was added dropwise 1.6 mL (11.2 mmol) of benzylchloroformate. The reaction mixture was stirred, at 0° C. under argon, for 1.5 hours. Thereafter, the reaction mixture was diluted with water and extracted with ethyl acetate. The ethyl acetate extracts were washed with saturated sodium chloride, dried over anhydrous Na$_2$SO$_4$, and concentrated under vacuum. The resulting residue was purified by flash chromatography using hexane:ethyl acetate (2:1) as an eluent to result in 2.5 g (71%) of N-(Benzyloxycarbonyl)-6-fluorotryptamine as a white solid. mp 72°–74° C.

$^1$H NMR (CDCl$_3$) δ67.4 (s, 5H), 7.6–6.8 (m, 4H), 5.2 (s, 2H), 3.5 (q, 2H), 2.9 (t, 2H).

IR (KBr) 3500–3200, 1700, 1510, 1480, 1450, 1250 Cm$^{-1}$. Analysis calculated for C$_{18}$H$_{17}$FN$_2$O$_2$: C, 69.22; H, 5.49; N, 8.99; F, 6.08 Found: C, 69.29; H, 5.25; N, 8.74; F, 5.86.

N-(P-Methoxybenzyloxycarbonyl)-5-fluorotryptamine

To a strirred suspension 1.4 g (7.8 mmol) of 5-fluorotryptamine in 5 mL of water and 1.1 mL (7.8 mmol) of triethylamine was added 2.5 g (7.8 mmol) of 2-(4-methoxybenzyloxycarbonyloxyimino)-2-phenylacetonitrile (MOZ-ON) and 10 mL of dioxane. The reaction mixture was stirred at room temperature for 1 hour under argon, diluted with water, and extracted with ethyl acetate. The organic extracts were washed with saturated sodium chloride, dried over anhydrous Na$_2$SO$_4$, and concentrated under vacuum. The residue was purified by flash chromatography, over silica gel, using hexane:ethyl acetate (2:1 and later 1:1) as eluents to provide 1.7 g (63%) of N-(p-methoxybenzyloxycarbonyl)-5-fluorotryptamine as an off-white solid. mp 118°–119° C.

$^1$H NMR (CDCl$_3$) δ7.5–6.8 (m, 8H), 5.15 (s, 2H), 3.8 (s, 3H), 3.5 (q, 2H), 2.9 (t, 2H).

IR (KBr) 3380, 3300) 1680, 1530, 1440, 1270 Cm$^{-1}$. Analysis calculated for C$_{19}$H$_{19}$FN$_2$O$_3$: C, 66.65; H, 5.59; N, 8.18 Found: C, 66.92; H, 5.69; N, 8.11.

N-Benzyloxycarbonyl-2-(para-fluorophenyl)ethylamine

Benzylchloroformate (12.2 g, 72 mmol) was added dropwise to a stirred solution, at 0° C., of 4-fluorophenylethyl amine (9.42 g, 72 mmol) in 50 mL of DMF. The mixture was stirred for an additional 3 hours at the same temperature. The reaction was quenched with water and extracted with 3×100 mL of ethyl acetate. The combined ethyl acetate extracts were washed with 2×100 mL of 5% HCl, water and dried over Na$_2$SO$_4$. Evaporation of the solvent resulted in a yellowish solid which was purified by recrystallization from ethyl acetate-hexane to furnish 8.6 g (46% yield) of N-Benzyloxycarbonyl-2-(parafluorophenyl)ethylamine. mp 51°–52° C.

$^1$H NMR (CDCl$_3$): δ7.4 (s, 5H), 7.2 (m, 4H), 5.2 (s, 2H), 4.9 (br s, 1H), 3.4 (q, 2H), 2.8 (t, 2H).

Analysis calculated for C$_{16}$H$_{16}$FNO$_2$: C, 70.33; H, 5.90; N, 5.13 Found: C, 70.23; H, 5.93; N, 5.14.

N-(para-Trifluoromethylbenzyloxycarbonyl)tryptamine

A solution of 1,1'-carbonyldiimidazole (2.03 g, 12.5 mmol), p-trifluoromethylbenzyl alcohol (2.2 g, 12.5 mmol) and THF (100 mL) was stirred for 2 hours. The reaction was monitored by TLC (silica gel, hexane:ethylacetate; 2:1) to examine the complete disappearence of p-trifluoromethylbenzyl alcohol. To this solution, 2.0 g (12.5 mmol) of tryptamine was added and the mixture was stirred overnight. The reaction contents were diluted with methylene chloride (100 mL). The organic layer was washed with 5% 3×100 mL of HCl, water (3×100 mL) and dried over anhydrous MgSO$_4$. Upon evaporation of the solvent, under vacuum, crude N-(para-Trifluoromethylbenzyloxycarbonyl)tryptamine was obtained as a solid which was crystallized from etherhexane mixture (2.6 g, 57% yield). mp 92°–94° C.

$^1$H NMR (CDCl$_3$): δ8.3 (br s, 1H), 7.5 (m, 9H), 5.2 (s, 2H), 3.5 (q, 2H), 2.9 (t, 2H).

Analysis calculated for C$_{19}$H$_{17}$F$_3$N$_2$O$_2$: C, 62.98; H, 4.73; N, 7.73 Found: C, 62.93; H, 4.74; N, 7.68.

N-(para-Nitrobenzyloxycarbonyl)-5-fluorotryptamine

To a stirred solution of 3.0 g (18.5 mmol) of 5-fluorotryptamine and 2.06 g (20.4 mmol) of ns methylmorpholine in 100 mL of methylene chloride at 0° C. was added dropwise a solution of 4.31 g (20.4 mmol) of p-nitrobenzylchloroformate in 20 mL of methylene chloride. The reaction mixture was stirred at 0° C. under argon, for 1.5 hours and then overnight at room temperature. The reaction mixture was filtered to remove the morpholine hydrochloride salt. The methylene chloride solution was washed with 5×100 mL 5% HCl and 3×100 mL water, dried over anhydrous Na$_2$SO$_4$. After the removal of the solvent under vacuum, a yellow solid was obtained which was crystallized from hot toluene (3.5 g, 53% yield). mp 93°–94° C.

$^1$H NMR (CDCl$_3$) δ8.3 (d, 2H), 7.8–6.9 (m, 7H), 5.2 (s, 2H), 3.3 (q, 2H), 2.9 (t, 2H).

IR (KBr) 3380, 3300, 2890, 2820, 1700, 1520, 1480, 1450, 1330, 1250 Cm$^{-1}$. Analysis calculated for C$_{18}$H$_{15}$FN$_3$O$_3$: C, 60.67; H, 4.24; N, 11.79 Found: C) 60.58; H, 4.60; N, 11.69.

N-(Cyclohexylmethyloxycarbonyl)-4-fluorophenylethyl amine

A solution of 4.87 g (30 mmol) of carbonyldiimidazole and 3.43 g (30 mmol) of cyclohexylmethanol was stirred, under nitrogen and at room temperature, for 2–4 hours or the time until the TLC (silica gel; hexane-ethylacetate, 4:1) analysis indicated a complete disappearance of cyclohexylmethanol in the mixture. To this reaction mixture, a solution of 4-fluorophenylethyl amine (4.18 g, 30 mmol) in methylene chloride (5 mL) was added and stirred overnight. The TLC analysis indicated a complete disappearence of 4-fluorophenylethyl amine. The reaction mixture was extracted with 4×50 mL of methylene chloride. The combined extracts were washed with 5% HCl (2×50 mL), water, dried over MgSO$_4$, and concentracted under vacuum. The solid was crystallized from hexane to furnish 5.0 g of N-(Cyclohexylmethyloxycarbonyl)-4-fluorophenylethyl amine (59% yield). mp 44°–45° C.

$^1$H NMR (CDCl$_3$) 67.18 (m, 4H), 5.0 (t, 1H), 3.95 (d, 2H), 3.45 (q, 2H), 2.87 (t, 2H), 1.68 (d, 5H), 1.21 (m, 6H).

IR (KBr) 3320, 2910, 2850, 1685, 1540, 1510, 1255, 1220, 1160, 860 Cm$^{-1}$. Analysis calculated for C$_{16}$H$_{22}$FNO2: C, 68.79; H, 7.94; N, 5.01 Found: C, 68.85; H, 7.93; N, 5.02.

2-Bromo-N-cyclopropylmethyloxycarbonyltryptamine

2-Bromo-N-cyclopropylmethyloxycarbonyltryptamine was prepared in two steps:

Step 1: Preparation of N-cyclopropylmethyloxycarbonyltryptamine:

A solution of 11.7 g (69.3 mmol) of carbonyldiimidazole and 5.0 g (69.3 mmol) of cyclopropylmethanol in 150 mL of THF was stirred, under nitrogen and later at room temperature for 4–5 hours or the time until the TLC (silica gel; hexane-ethylacetate, 4:1) analysis indicated a complete disappearance of cyclopropylmethanol in the mixture. To this reaction mixture, a solution of tryptamine (11.12 g, 69.3 mmol) in THF (5 mL) was added and stirred overnight. The TLC analysis indicated a complete disappearence of tryptamine. The solvent was removed and the residue was redissolved in methylene chloride (450 mL), washed with 5% HCl (4×100 mL), water, dried over MgSO$_4$, filtered. The filtrate was swirled with 50 g of silica gel, filtered and concentracted under vacuum. The solid was crystallized from hexane-methylene chloride to furnish 13.6 g of N-cyclopropylmethyloxycarbonyltryptamine (75% yield). mp 88°–90° C.

$^1$H NMR (CDCl$_3$) δ8.4 (br s, 1H), 7.8–7.0 (m, 5H), 4.9 (br s, 1H), 3.9 (d, 2H), 3.6 (q, 2H), 3.0 (t, 2H), 1.1 (m, 1H), 0.5 (m, 2H), 0.3 (m, 2H).

IR (KBr) 3300, 1660, 1540, 1460, 1250, 1145, 1025, 740 Cm$^{-1}$. Analysis calculated for C$_{15}$H$_{18}$N$_2$O$_2$: C, 69.7; H, 6.97; N, 10.84 Found: C, 69.83; H, 7.02; N, 10.83.

Step 2: 2-Bromo-N-cyclopropylmethyloxycarbonyl-tryptamine

To a cold (−10° C.) solution of 5.5 g (21 mmol) of N-cyclopropylmethyloxy-carbonyltryptamine in 10 mL of glacial acetic acid, under nitrogen, 3.8 g (21 mmol) of N-bromosuccinimide was added in one lot. The mixture was stirred at −10° C. for 1.5 hours. The reaction was quenched with 200 mL of water and extracted with 3×100 mL of methylene chloride. The methylene chloride extracts were washed with 2×100 mL water, saturated NaCl solution, and dried over anhydrous magnesium sulfate. The solvent was removed under vacuum to furnish 6.3 g of a crude mixture which showed several spots on the TLC plate (silica gel plate eluted in hexane-ethyl acetate, 1:1 mixture). Repeated column chromatography over silica gel and elution with hexane-ethyl acetate (1:1) resulted 0.3 g of the pure product. mp 124°–126° C.

$^1$H NMR (CDCl$_3$-90 MHz) δ8.5 (br s, 1H), 7.8 (s, 1H), 7.3 (s, 2H), 7.1 (s, 1H), 4.8 (br s, 1H), 3.9 (d, 2H), 3.5 (m, 2H), 2.9 (t, 2H), 1.1 (m, 1H), 0.5 (m, 2H), 0.3 (m, 2H)

IR (Neat): 3300, 1660, 1540, 1460, 1450, 1280, 1260, 1140, 970, 880 Cm$^{-1}$ Analysis calculated for C$_{15}$H$_{17}$BRN$_2$O$_2$: C, 53.43; H, 5.08; N, 8.31; Br, 23.70 Found: C, 53.64; H, 5.10; N, 8.28; Br, 23.54.

The Synthesis of N-[(R & S)-mandeloyl]tryptamine:

The general procedure for making amide from mandelic acid and tryptamine was not successful. A novel method for the synthesis of such amides was developed. This method consists of the following two steps. In the first step, an activated ester of mandelic acid and 3-hydroxy-1,2,3-benzotriazin-4(3H)-one (HO-Dhbt, available from Aldrich Chemical Co.) was made. In the second step, the activated ester was reacted with the tryptamine to result in the required N-[(R & S)-mandeloyl]tryptamine.

Activated Ester of (R & S)-mandelic acid and HO-Dhbt:

Mandelic acid (2.0 g, 13.14 mmol) was dissolved in 50 mL of THF in a round bottom flask and the solution was cooled down to −15° C. Dicyclohexylcarbodimide (DCC, 2.71 g, 13.14 mmol) was added to the flask and the reaction was stirred for 5 minutes at −15° C. Solid HO-Dhbt (2.14 g, 13.14 mmol) was added to the reaction flask and the contents were stirred at −10° C. for 30 minutes and at 0° C. for 4 hours. After standing overnight at 0° C., the solid precipitates of dicyclourea were removed by filtration. After the removal of the solvent, the oil was crystallized from hexane-ether. The analyses for the activated esters were as follows:

| Activated ester of HO-Dhbt | mp, °C. | Rf, TLC |
|---|---|---|
| R-Mandelic acid | 125–127 | 0.88 (EtOAc—MeOH; 7:3) |
| S-Mandelic acid | 127–129 | 0.5 (EtOAc—MeOH; 1:1) |

N-[(R & S)-mandeloyl]tryptamine:

During stirring, tryptamine (1.07 g, 6.7 mmol) was added to the above HO-Dhbt-ester of the mandelic acid which was dissolved in THF (25 mL). The reaction contents were stirred, under nitrogen, at room temperature for 3 hours. The solvent was evaporated under vacuum and the resulting light brown solid was dissolved in dichloromethane. The dichloromethane solution was successively washed with 1×100 mL of 5% HCl, 1×100 mL of 5% sodium bicarbonate solution, 2×100 mL of deionized water, 1×100 mL of saturated sodium chloride solution, and dried over anhydrous magnesium sulfate. The solid, obtained after the evaporation of solvent, was crystallized from ethyl acetate-hexane mixture. The analyses for the N-[(R & S)-mandeloyl]tryptamine were as follows:

| N-[mandeloyl]-tryptamine | mp, °C. | Rf, TLC | Elemental Analysis | | | | | |
|---|---|---|---|---|---|---|---|---|
| | | | Calcd | | | Found | | |
| | | | C | H | N | C | H | N |
| N-[(R)-mandeloyl]-tryptamine | 142–143 | 0.5 (EtOAc—MeOH; 1:1) | 73.45 | 6.16 | 9.52 | 73.31 | 6.31 | 9.51 |
| N-[(S)-mandeloyl]-tryptamine | 141–143 | 0.55 (EtOAc—MeOH; 1:1) | 73.45 | 6.16 | 9.52 | 73.54 | 6.18 | 9.44 |

By adjusting the synthetic parameters described above, a variety of novel substituted compounds of the present invention, having therapeutic properties, may be obtained.

Examples of compounds to which the present invention is directed are represented below in Tables I–V. As demonstrated by the data provided in these Tables, for example, the compounds of the present invention possess unexpectedly high degrees of activity.

All compounds included in the following table were tested in the hexobarbital-induced loss of righting reflex assay, a screen for sedative activity. Male Swiss Webster mice, 20–30 g, were injected intraperitoneally (10 ml/kg) with either vehicle (5% dimethylformamide, 10% polyoxyethylene-sorbital monooleate [Tween 80], water) or 3, 10, 30 or 100 mg/kg test compound in vehicle. Ten mice were used for each group. Ten minutes later the mice received 120 mg/kg hexobarbital (in 10% Tween/water, 10 ml/kg i.p.). Once the righting relex was lost, animals were placed on their backs on "Thermal Barrier" pads (24°–25° C., Vetco). Upon recovery of the righting reflex, the duration of time since hexobarbital administration was recorded. Dose groups were compared using a one-way analysis of variance (SigmaStat ™ statistical software). If significance was reached ($p \leq 0.05$), the Student-Newman-Keuls test was applied to determine which groups were significantly different from the vehicle control group. In the tables, the lowest dose that was significantly different from the control is indicated as the activity of the compound. Compounds that did not increase hexobarbital-sleep time at doses up to 100 mg/kg are noted with "—" in the activity column. Some of the compounds exhibited toxicity, and this is noted by an asterisk in the activity column. Toxicity was defined as more than one death per dose group, and additional deaths in higher dose groups.

TABLE 1

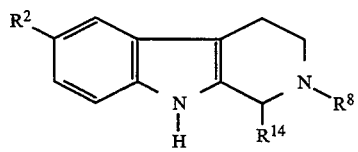

| IP Number | $R^2$ | $R^{14}$ | $R^8$ | Activity |
|---|---|---|---|---|
| 100-4 | $OCH_3$ | $CH_3$ | H | "—" |
| 100-5 | H | phenyl | H | 10* |
| 100-6 | H | 4-methylphenyl | $COCH_3$ | 100 |
| 100-20 | benzyl | phenyl | H | 100* |

TABLE 2

Phenylethylamine Derivative

| IP # | $R^2$ | $R^3$ | $R^{10}$ | Activity, mg/kg |
|---|---|---|---|---|
| IP-100-7 | H | H | OCH₂-phenyl | 30 |
| IP-100-10 | H | H | CH₂-phenyl | 100 |
| IP-100-22 | H | F | CH₂-phenyl | 10* |
| IP-100-23 | F | H | CH₂-phenyl | 3* |
| IP-100-24 | F | H | OCH₂-phenyl | 30 |

TABLE 2-continued

Phenylethylamine Derivative

| IP # | R² | R³ | R¹⁰ | Activity, mg/kg |
|---|---|---|---|---|
| IP-100-25 | H | F | benzyloxy (OCH₂-C₆H₅) | 10 |
| IP-100-26 | F | H | 4-fluorobenzyloxy | 30 |
| IP-100-27 | H | F | 4-fluorobenzyloxy | 10* |
| IP-100-28 | H | F | 4-(trifluoromethyl)benzyloxy | 3 |
| IP-100-29 | F | H | 4-(trifluoromethyl)benzyloxy | 10 |
| IP-100-32 | H | F | 4-chlorobenzyloxy | 10* |
| IP-100-33 | H | F | 4-methylbenzyloxy | 30 |
| IP-100-34 | H | F | 3,4-dimethylbenzyloxy | 30* |
| IP-100-40 | H | F | (1,3-benzodioxol-5-yl)methoxy | 3* |
| IP-100-44 | H | F | 4-isopropylbenzyloxy | 30 |
| IP-100-49 | H | F | (S)-1-(4-nitrophenyl)pyrrolidin-2-ylmethoxy | 100 |
| IP-100-50 | H | F | cyclohexylmethoxy | 3 |
| IP-100-62 | H | F | 4-(trifluoromethyl)benzyl (CH₂-C₆H₄-CF₃) | 30* |
| IP-100-66 | F | H | 4-fluorobenzyl | 100 |
| IP-100-67 | H | F | 4-fluorobenzyl | 100 |

TABLE 3

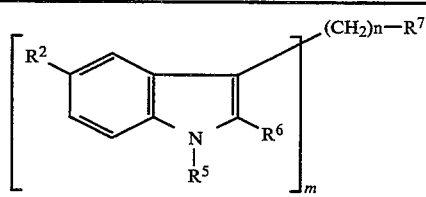

| IP Number | "m" | R² | R⁵ | R⁶ | (CH₂)ₙ—R⁷ | Activity, mg/kg |
|---|---|---|---|---|---|---|
| IP-100-11 | 1 | H | H | H | 1-(1H-tetrazol-5-yl)ethylidene | "—" |

TABLE 3-continued $$\left[\begin{array}{c} R^2 \\ \\ \\ N \\ | \\ R^5 \end{array}\text{indole ring with } R^6 \text{ at 2-position}\right]_m \!\!- (CH_2)_n - R^7$$

| IP Number | "m" | $R^2$ | $R^5$ | $R^6$ | $(CH_2)_n$—$R^7$ | Activity, mg/kg |
|---|---|---|---|---|---|---|
| IP-100-12 | 1 | H | —CH₂—C₆H₅ | H | 5-methyl-1-benzyl-tetrazol-1-yl | "—" |
| IP-100-13 | 1 | H | —CH₂—C₆H₅ | H | 5-methyl-2-benzyl-tetrazol-2-yl | "—" |
| IP-100-14 | 1 | H | —CH₂—C₆H₅ | H | 5-methyl-tetrazol-2-yl-H | 30 |
| IP-100-15 | 1 | H | —CH₂—C₆H₅ | H | isopropyl-O-N(CH₃)- oxadiazole | "—" |
| IP-100-19 | 1 | H | —COCH₃ | H | isopropyl-O-N(CH₃)- oxadiazole | "—"* |
| IP-100-53 | 1 | H | H | H | —CH₂—CO—NH—CH(d)(CH₂C₆H₅)—CO₂H | "—"* |
| IP-100-54 | 1 | H | H | H | —CH₂—CO—NH—CH₂—C₆H₅ | 100 |
| IP-100-56 | 1 | H | H | H | —CH₂—CO—NH—SO₂—C₆H₅ | 100* |
| IP-100-63 | 1 | H | H | —CH₂—C₆H₅ | —CH₂—CH₂—NH₂ | 30* |
| IP-100-68 | 1 | OCH₃ | H | —CH₂—C₆H₅ | —CH₂—CH₂—NH₂ | 3* |

TABLE 3-continued

Structure: indole with R² at 5-position, R⁵ on N, R⁶ at 2-position, and (CH₂)ₙ—R⁷ at 3-position, bracketed with subscript m.

| IP Number | "m" | R² | R⁵ | R⁶ | (CH₂)ₙ—R⁷ | Activity, mg/kg |
|---|---|---|---|---|---|---|
| IP-100-69 | 1 | F | H | H | —CH₂—CH₂—NH—CO—NH—CH₂—(phenyl) | "—" |
| IP-100-70 | 2 | H | H | H | —NH—CO—O—CH₂—(cyclohexyl)—CH₂—O—CONH— | "—" |
| IP-100-71 | 1 | H | H | H | —CH₂—CO—NH—(phenyl) | 30 |
| IP-100-72 | 2 | H | H | H | —NH—CO—O—(CH₂)₈—O—CO—NH— | "—" |

TABLE 4

Structure: indole with R² and R³ on benzene ring, R⁵ on N, R⁶ at 2-position, and —CH₂CH₂—N(H)—C(=O)—R¹⁰ at 3-position.

| IP # | R² | R³ | R⁵ | R⁶ | R¹⁰ | Activity, mg/kg |
|---|---|---|---|---|---|---|
| IP-100-41 | CH₃O | H | H | H | Cyc—Pr (cyclopropyl) | 10* |
| IP-100-42 | OCH₃ | H | H | H | CF₃ | 10* |
| IP-100-57 | H | H | H | H | CH₃O/H—C(R)—phenyl | 30 |
| IP-100-58 | H | H | H | H | CH₃O/H—C(S)—phenyl | 30 |
| IP-100-64 | H | H | H | H | OH/H—C(R)—phenyl | 100 |
| IP-100-65 | H | H | H | H | OH/H—C(S)—phenyl | "—" |

TABLE 5
Tryptamine-CARBAMATE (INDLCARB.TBL)

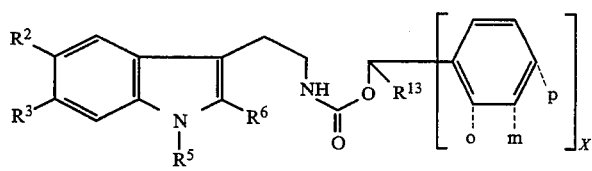

| IP # | R² | R³ | R⁵ | R⁶ | R¹³ | o--- | m--- | p--- | X | Activity, mg/kg |
|---|---|---|---|---|---|---|---|---|---|---|
| IP-100-1 | H | H | H | H | H | H | H | OCH₃ | 1 | 10 |
| IP-100-2 | CH₃O | H | H | H | H | H | H | H | 1 | 100 |
| IP-100-3 | CH₃O | H | H | H | H | H | H | OCH₃ | 1 | 100 |
| IP-100-8 | HO | H | H | H | H | H | H | H | 1 | "—" |
| IP-100-9 | F | H | H | H | H | H | H | H | 1 | 10 |
| IP-100-16 | H | F | H | H | H | H | H | H | 1 | 10 |
| IP-100-17 | F | H | H | H | H | H | H | OCH₃ | 1 | 10 |
| IP-100-18 | F | H | H | H | H | H | H | F | 1 | 3* |
| IP-100-21 | Cl | H | H | H | H | H | H | H | 1 | 10* |
| IP-100-30 | H | H | H | H | H | H | H | Cl | 1 | 3* |
| IP-100-31 | H | H | H | H | H | H | H | CH₃ | 1 | 10* |
| IP-100-35 | H | H | H | H | H | H | H | CH(CH₃)₂ | 1 | 100 |
| IP-100-36 | H | H | H | H | H | H | CH₃ | CH₃ | 1 | 30 |
| IP-100-37 | H | H | H | H | H | H | H | CF₃ | 1 | 3 |
| IP-100-38 | F | H | H | H | H | H | H | NO₂ | 1 | 3 |
| IP-100-39 | H | H | H | H | H | (O-CH₂-O methylenedioxy) | | | 1 | 30 |
| IP-100-43 | H | H | H | H | S—CH₃ | H | H | H | 1 | 10 |
| IP-100-45 | OCH₃ | H | H | H | CH₂-cyclopropyl | | | | 0 | 30 |
| IP-100-46 | H | H | H | H | R—CH₃ | H | H | H | 1 | 10* |
| IP-100-47 | H | H | H | Br | H | H | H | H | 1 | 30* |
| IP-100-48 | H | H | H | H | (S)-2-methyl-1-(4-nitrophenyl)pyrrolidine | | | | 0 | "—" |
| IP-100-51 | F | H | H | H | CH₂-cyclopentyl | | | | 0 | 100 |
| IP-100-52 | F | H | H | H | CH₂-cyclobutyl | | | | 0 | 100 |
| 100-59 | H | H | H | H | cyclopropyl | | | | 0 | 100* |
| 100-60 | H | H | H | Br | cyclopropyl | | | | 0 | 10 |
| 100-61 | F | H | H | Br | H | H | H | H | 1 | |

UTILITY

The compounds of the present invention are generally useful in the treatment of indications including (but not limited to): 1. chronobiological-based disorders (e.g., jet lag, delayed sleep syndrome, shift-work, seasonal affective disorder); 2. central nervous system and psychiatric disorders (e.g., sleep disorders, epilepsy and other convulsive disorders, anxiety, psychiatric diseases, neurodegenerative diseases, fever); 3. endocrine indications (e.g, contraception and infertility, precocious puberty, premenstrual syndrome, hyperprolactinemia, growth hormone deficiency); 4. cancer and other proliferative diseases; 5. immune system disorders and conditions associated with senescence; 6. ophthalmological diseases; and 7. animal breeding (e.g., regulation of fertility, puberty, pelage color).

Compounds of the present invention are useful as sedatives or hypnotics. These activities were measured using generally accepted techniques known to those skilled in the art. For instance, the activity of compounds useful as sedatives or hypnotics can be measured using a barbituate-induced loss of righting reflex assay (e.g. Hermansen, Acta Pharmacol. Toxicol. 27:453–460, 1969), which is hereby incorporated by reference in its entirety, and as described below. Another assay which is useful for predicting sedative activity is the generally accepted Rotarod Assay, which is described in Watzman et al., Arch. Int. Pharmacodyn. Ther. 169:362–374, 1967, which is hereby incorporated by reference in its entirety, and as described below.

Hexobarbital Sleep Assay

A known effect of sedatives and hypnotics is to potentiate the hypnotic effects of a barbituate, like hexobarbital, in mice. Mice will stay on their backs (loss of righting reflex) when given hexobarbital. Increases in sleep duration (loss of righting reflex) indicate sedative/hypnotic activity. Increases in the length of time the mice remain on their backs predict sleep-inducing compounds.

Figure 2:
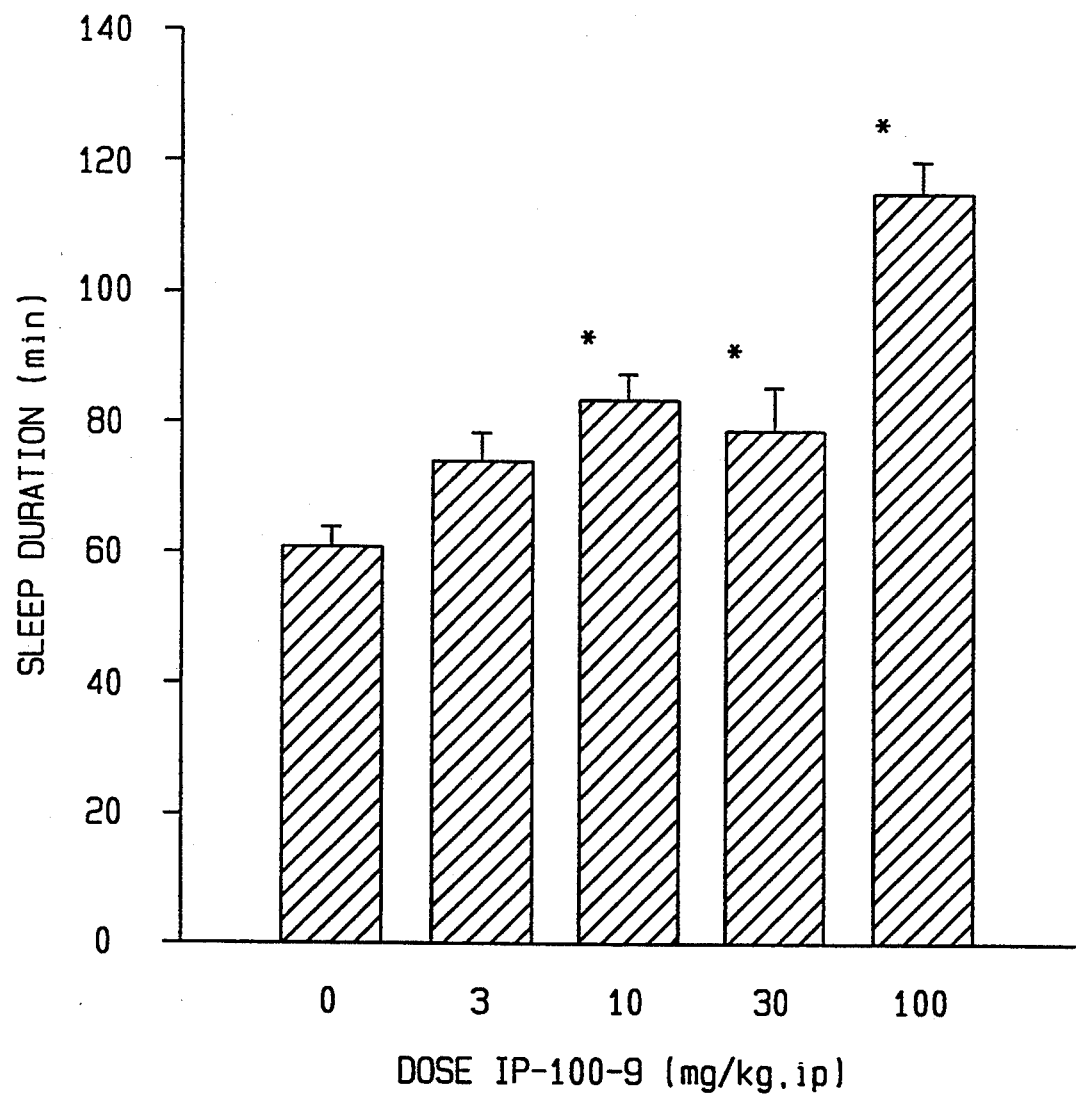
FIG. 2 is a bar graph showing the effect of various intraperitoneal dosages of N-(benzyloxycarbonyl)-5-fluoro tryptamine, the composition of IP-100-9, on the duration of hexobarbital-induced sleep in mice.
Figure 3:
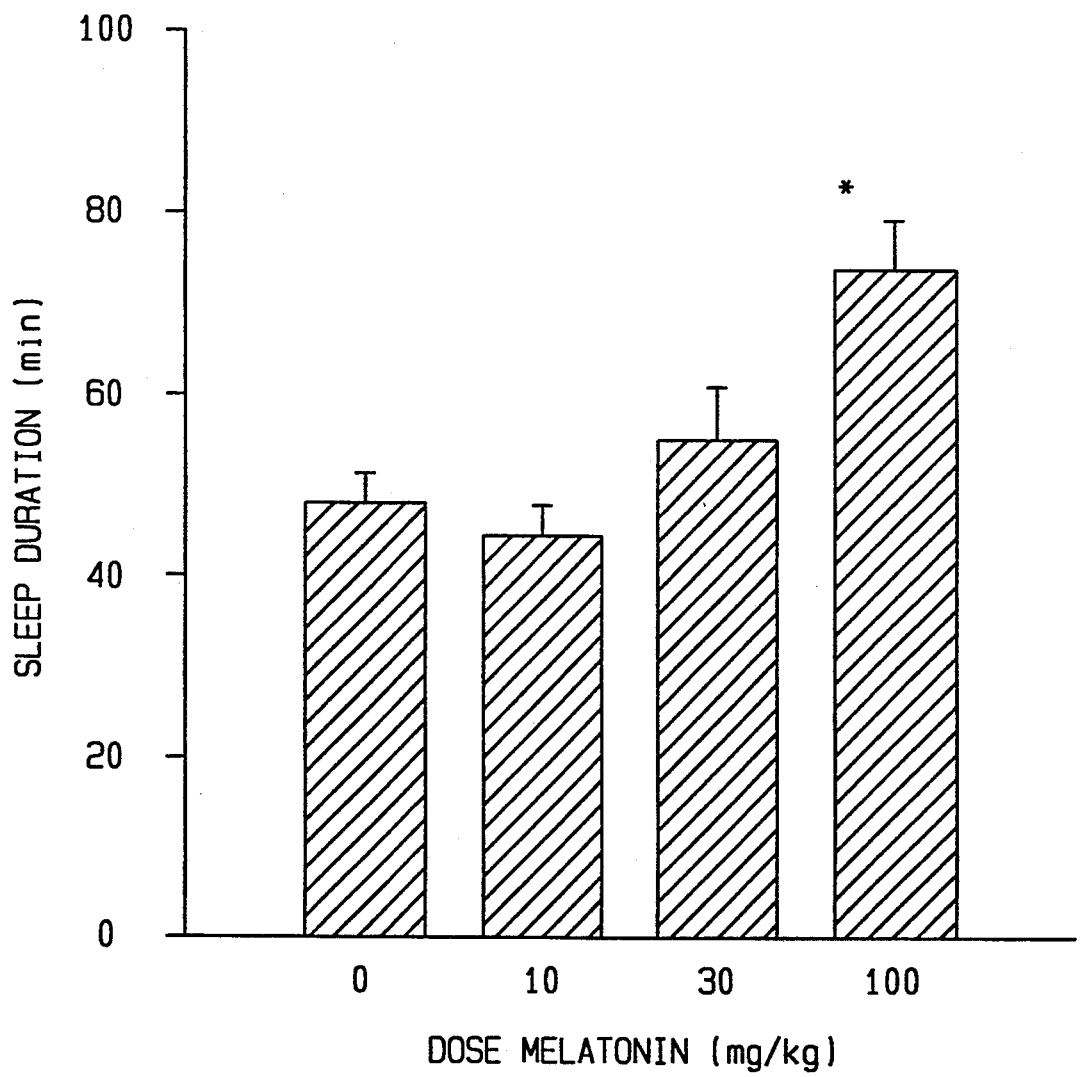
FIG. 3 is a bar graph showing the effect of various orally administered dosages of melatonin on the duration of hexobarbital-induced sleep in mice.
Figure 4:
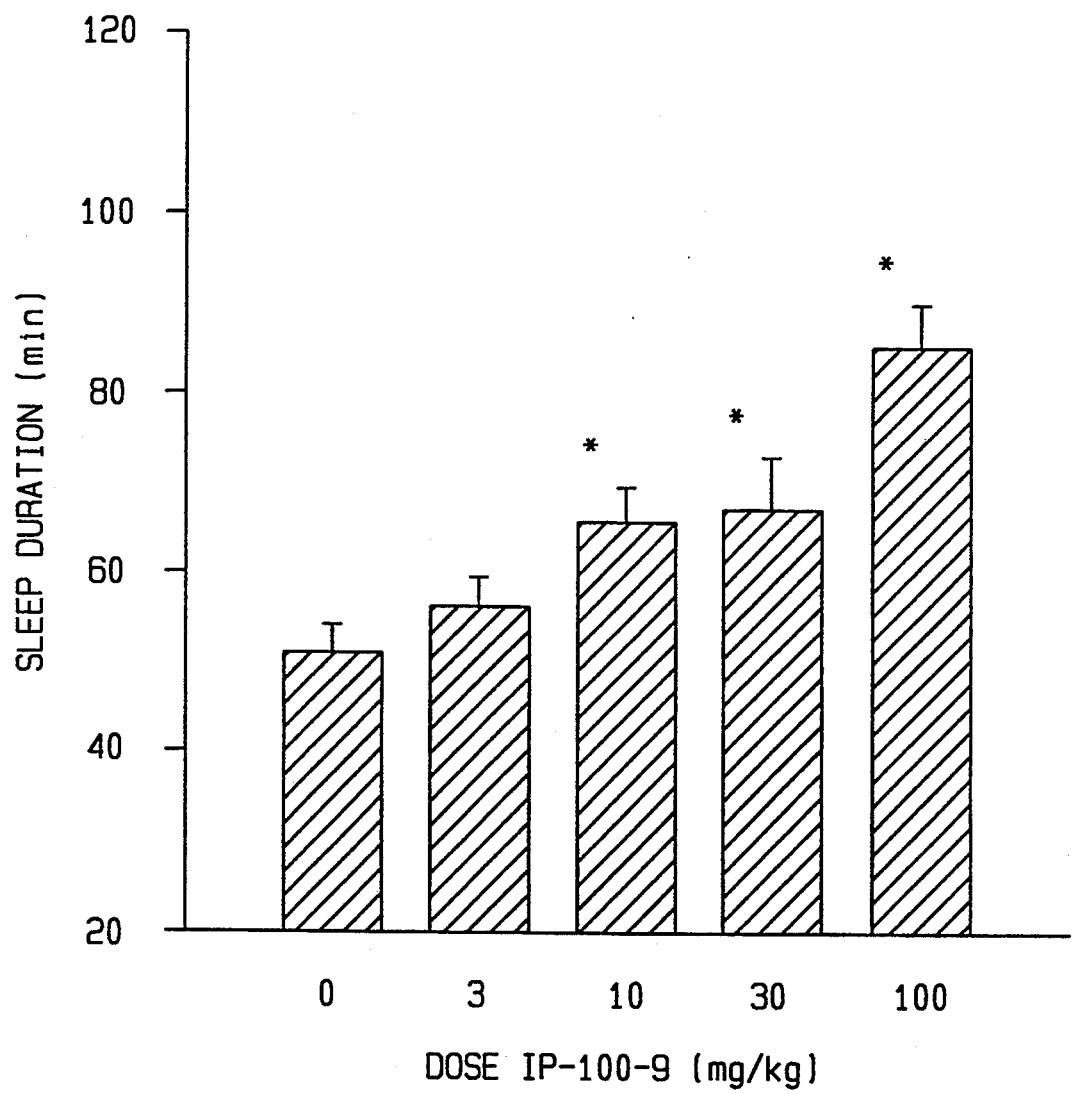
FIG. 4 is a bar graph showing the effect of various orally administered dosages of N-(benzyloxycarbonyl)-5-fluoro tryptamine, the composition of IP-100-9, on the duration of hexobarbital-induced sleep in mice.

Various doses of (1) melatonin and (2) IP-100-9 were administered intraperitoneally (FIGS. 1 and 3) and orally (FIGS. 2 and 4), followed after 10 minutes by intraperitoneal injection of 120 mg/kg hexobarbital. The latency to recovery of righting (i.e. "sleep time") was then measured. When introduced intraperitoneally, the minimum effective dose of melatonin was 30 mg/kg, whereas for IP-100-9 it was 10 mg/kg. Melatonin was much less potent when administered orally. Thus the required oral dosage of melatonin to obtain a significant effect was 100 mg/kg, whereas, in contrast, for IP-100-9, it was again 10 mg/kg.

Forced Motor Activity:

Rotarod Assay

Figure 5:
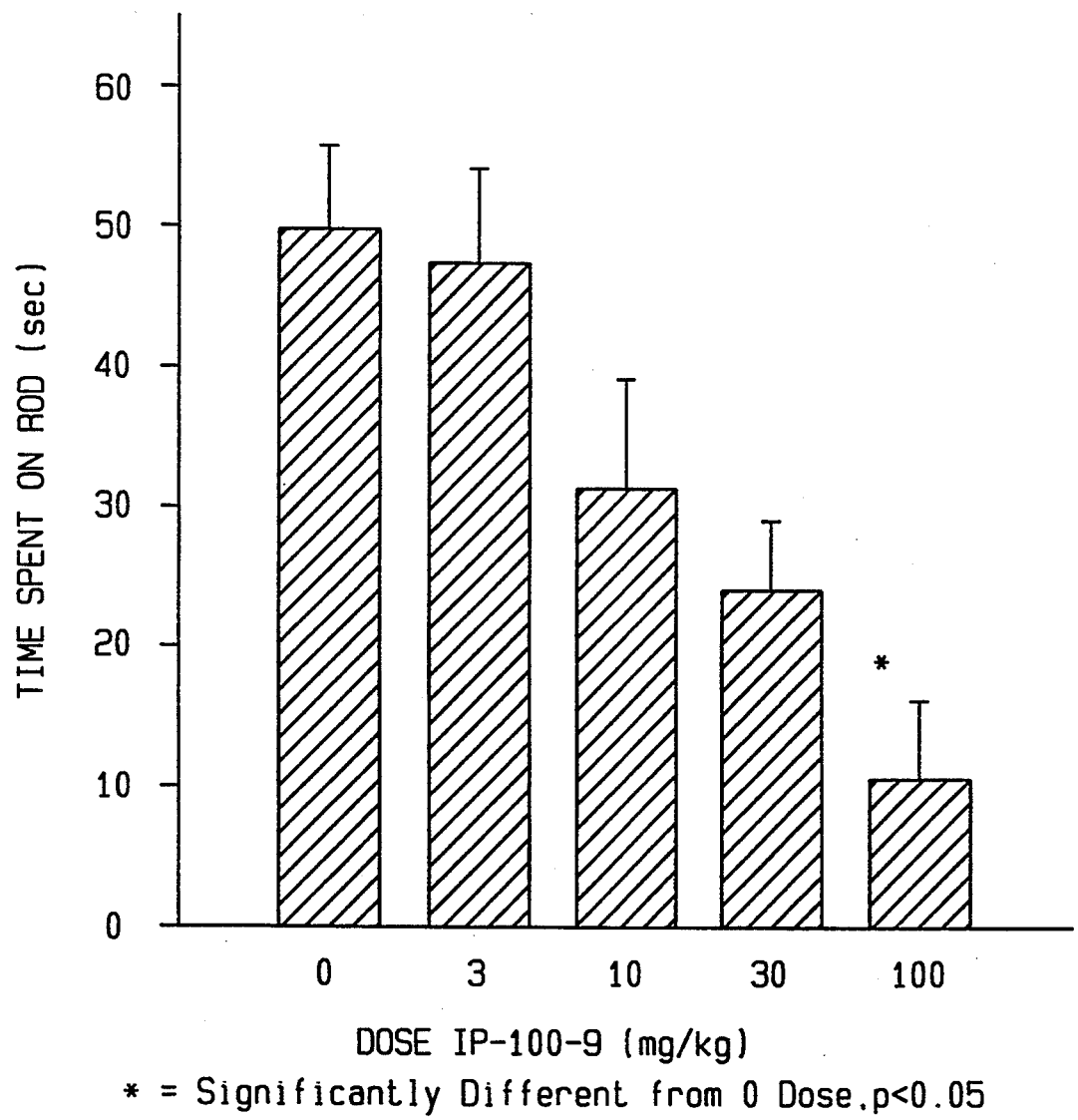
FIG. 5 is a bar graph showing the effect of various melatonin dosages upon the ability of a mouse to remain upon a rotating rod.
Figure 6:
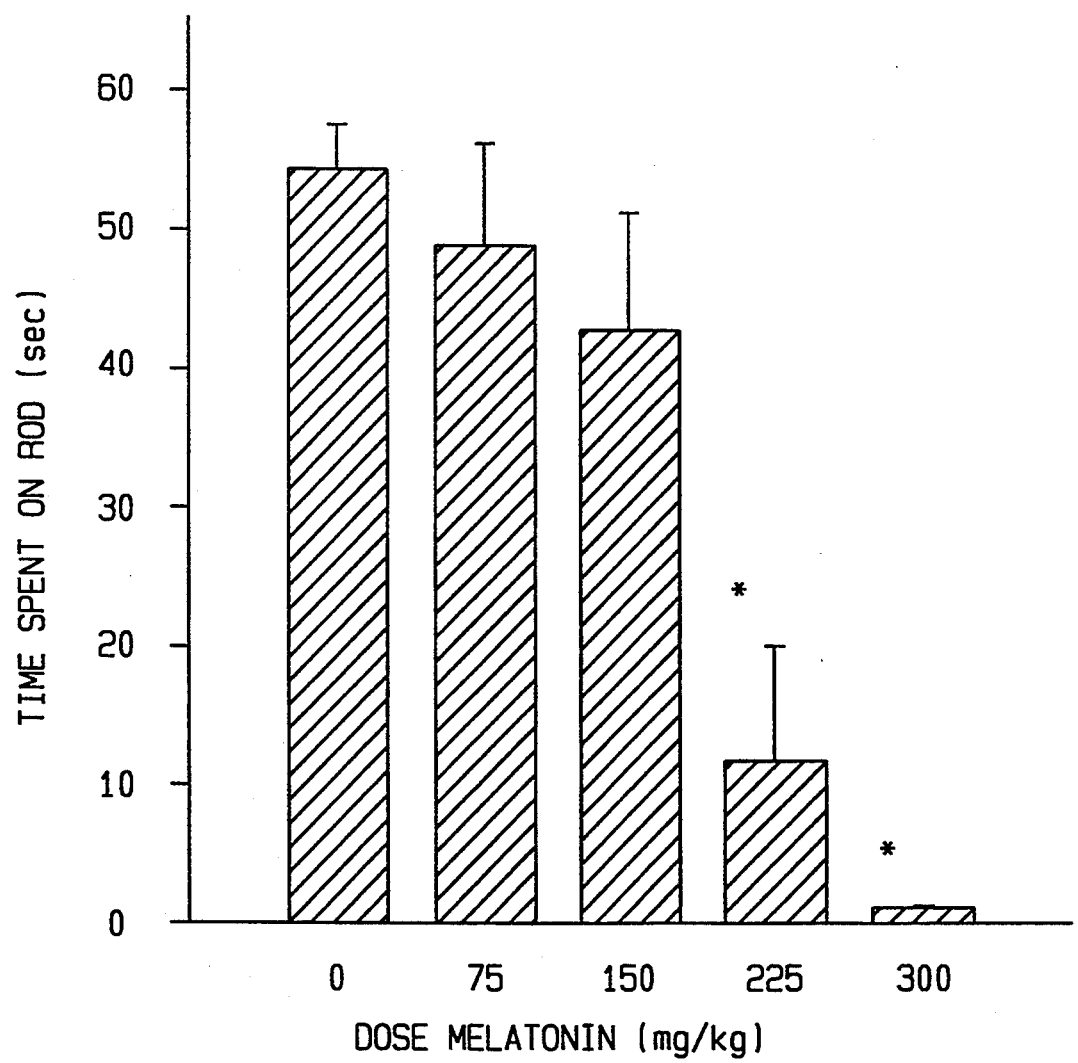
FIG. 6 is a bar graph showing the effect of various dosages of N-(benzyloxycarbonyl)-5-fluoro tryptamine, the composition of IP-100-9, upon the ability of a mouse to remain upon a rotating rod.

Mice were injected intraperitoneally with varying dosages of (1) melatonin or (2) IP-100-9 and were thereafter placed upon a slowly rotating rod (6 r.p.m.). The length of time the mice are able to remain upon the rod up to a maximum of 60 seconds is an indication of the sedative effect of these compounds. As shown in FIG. 5, no significant effect was seen with melatonin until a dosage of 225 mg/kg was administered. In contrast, as demonstrated in FIG. 6, administration of only 30 mg/kg of IP-100-9 was required in order to obtain a significant effect.

The results indicate that compounds of the present invention possess sedative/hypnotic activity.

DOSAGE AND FORMULATION

Compounds of formulae I and II can be administered by any means that produces contact of the active agent with the agent's site of action in the body of a subject. They can be administered by any conventional means available for use in conjunction with pharmaceuticals, either as individual therapeutic agents or in combination with other therapeutic agents. They can be administered alone, but are generally administered with a pharmaceutical carrier selected on the basis of the chosen route of administration and standard pharmaceutical practice. The pharmaceutical compositions of the invention may be adapted for oral, parenteral, rectal, transdermal and nasal administration, and may be in unit dosage form, as well known to those skilled in the pharmaceutical art.

In general, a pharmacologically effective daily dose can be from about 0.01 mg/kg to about 25 mg/kg per day, bearing in mind, or course, that in selecting the appropriate dosage in any specific case, consideration must be given to the subject's weight, general health, metabolism, age and other factors which influence response to the drug.

Preferred embodiment of this invention is the provision of pharmaceutical compositions in dosage unit form which comprise from about 0.5 mg to about 500 mg of a compound of the above formulae.

The active ingredient can be administered orally in solid dosage forms, for example, as tablets, capsules or powders, or in liquid dosage forms, such as aqueous or oily suspensions, disperse powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets.

These excipients may be, for example, inert diluents, such as calcium carbonate, sodium carbonate, lactose, calcium phosphate, or sodium phosphate; granulating disintegrating agents, e.g., maize starch, or alginic acid; binding agents, such as starch, gelatin, or acacia; and lubricating agents, for example, magnesium stearate, stearic acids or talc. The tablets may be uncoated or they may be coated by known techniques to delay disintegration and adsorption in the gastrointestinal tract. Thereby a sustained action over a longer period can be provided.

Formulations for oral use can also be presented as hard gelatin capsules wherein the active ingredient is mixed with an inert solid diluent, e.g., calcium carbonate, calcium phosphate, or kaolin, or as soft gelatin capsules wherein the active ingredient is mixed with an oil medium, such as arachis oil, liquid paraffin or olive oil.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acadia; dispersing or wetting agents, such as a naturally-occurring phosphatide, e.g., lecithin, or condensation products of an alkylene oxide with fatty acids, for example of polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Disperse powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents. The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc. with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

The pharmaceutical compositions can be tableted or otherwise formulated so that for every 100 parts by weight of the composition there are present between 5 and 95 parts by weight of the active ingredient. The dosage unit form will generally contain between 0.5 mg and about 500 mg of the active ingredient of the formula stated above.

From the foregoing formulation discussion, it is apparent that the compositions of this invention can be administered orally, transdermally, transmucosally, or parenterally. The term parenteral as used herein includes subcutaneous injection, intravenous, intramuscular, or intracisternal injection or infusion techniques.

All references cited in the present application are incorporated by reference in their entirety.

The foregoing disclosure includes all the information deemed essential to enable those skilled in the art to practice the claimed invention. Various modifications of the invention in addition to those shown and described herein will be apparent to those skilled in the art from the foregoing description. Such modifications are also intended to fall within the scope of the appended claims.

We claim:

1. A compound of the following formula

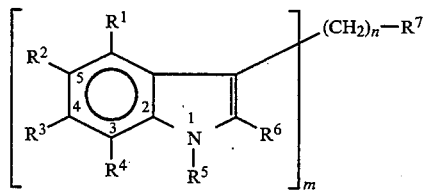

wherein:

$R^1$, $R^2$, $R^3$ and $R^4$ are independently hydrogen, halogen, hydroxy, alkoxy or alkyaryl;

$R^5$ is hydrogen, alkyl, alkylaryl or acetyl;

$R^6$ is hydrogen, alkyl, alkylaryl or halogen;

n is 0 to 2;

m is 1 to 2;

$R^7$ is —$NHR^8$,

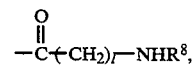

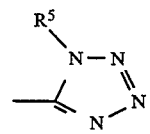

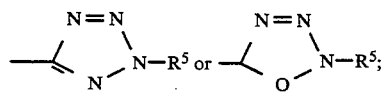

l is 0 to 2;

$R^8$ is hydrogen,

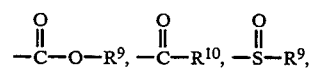

or $R^9$;

$R^9$ is alkylene, aryl, alkylaryl, alkylcycloalkyl,

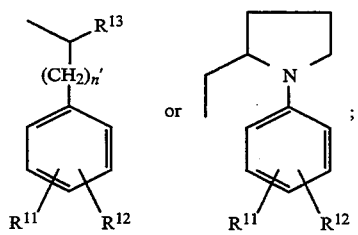

$R^{10}$ is cycloalkyl, $CF_3$, $CH_3$,

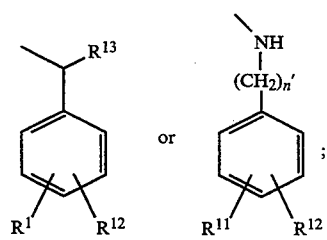

$R^{11}$ and $R^{12}$ are hydrogen; and

R¹³ is alkyoxy, hydroxy, hydrogen, thioalkyl, alkylcycloalkyl or

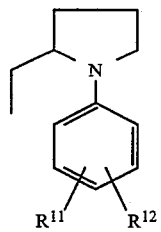

n' is 0 to 2;
with the proviso that if R⁶ is hydrogen, R⁷ is —NHR⁸ and
R⁸ is

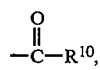

then R¹³ is not hydrogen; if n is 2, then R¹⁰ is not cycloalkyl, CF₃ or

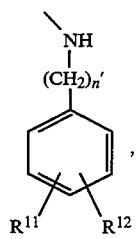

where n' is 1 to 2; if m is 1, R⁹ is not alkylene.

2. A compound of claim 1 having the following formula:

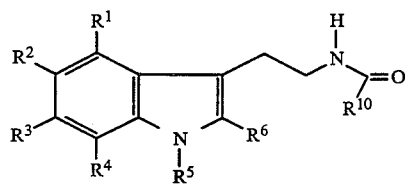

wherein:
R¹, R², R³ and R⁴ are independently hydrogen, halogen hydroxy or alkoxy;
R⁵ is hydrogen;
R⁶ is hydrogen or halogen;
x is 0 or 1;
R¹¹ and R¹² are independently hydrogen, —NO₂, alkoxy, CF₃, alkyl, halogen or R¹¹ taken together with R¹² is

and
R¹³ is hydrogen, thioalkyl, alkylcycloalkyl or

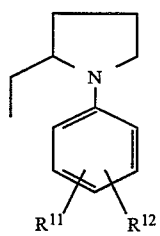

with the proviso that if R⁶ is hydrogen, R¹³ is not hydrogen.

3. A compound of claim 1 having the following formula:

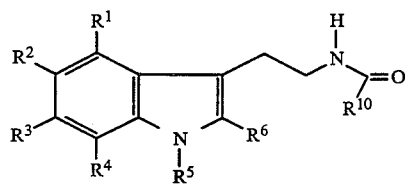

wherein R¹, R², R³ and R⁴ are independently hydrogen or alkoxy;
R⁵ is hydrogen;
R⁶ is hydrogen;
R¹⁰ is

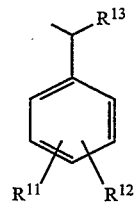

or

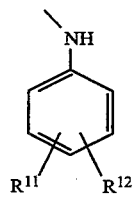

R¹¹ and R¹² are hydrogen; and
R¹³ is alkoxy or hydroxy.

4. A compound which is:
N-(p-Methoxybenzyloxycarbonyl)tryptamine;
N-(Benzyloxycarbonyl)-5-methoxytryptamine;
N-(p-methoxybenzyloxycarbonyl)-5-methoxytryptamine;

N-(Benzyloxycarbonyl)-5-hydroxytryptamine;
N-(Benzyloxycarbonyl)-5-fluorotryptamine;
3-(5-tetrazolyl)indole;
1-benzyl-3-(1-benzyl-5-tetrazolyl)indole;
1-benzyl-3-(2-benzyl-5-tetrazolyl)indole;
1-benzyl-3-(5-tetrazolyl)indole;
1-benzyl-3-[5-2-methyl-1,3,4-oxadiazolyl)indole;
N-(Benzyloxycarbonyl)-6-fluorotryptamine;
N-(p-methoxybenzyloxycarbonyl)-5-fluorotryptamine;
N-(4-Fluorobenzyloxycarbonyl)-5-fluorotryptamine;
1-acetyl-3-[5-2-methyl-1,3,4 oxadiazolyl)indole;
N-(Benzyloxycarbonyl)-5-chlorotryptamine;
N-(p-Chlorobenzyloxycarbonyl)tryptamine;
(p-Methylbenzyloxycarbonyl)tryptamine;
N-(p-Isopropylbenzyloxycarbonyl)tryptamine;
N-(3,4-Dimethylbenzyloxycarbonyl)tryptamine;
N-(p-Trifluoromethylbenzyloxycarbonyl)tryptamine;
N-(p-Nitrobenzyloxycarbonyl)-5-fluorotryptamine;
N-(3,4-methylenedioxybenzyloxycarbonyl)tryptamine;
N-[(S)-α-Methylbenzyloxycarbonyl]tryptamine;
N-Cyclopropanemethyloxycarbonyl)-5-methoxytryptamine;
N[(R)-α-methylbenzyloxycarbonyl]tryptamine;
2-Bromo-N-(Benzyloxycarbonyl)tryptamine;
N-[(S)-(−)-1,4-(nitrophenyl)-2-pyrrolidinemethyloxycarbonyl]tryptamine;
N-Cyclopentylmethyloxycarbonyl-5-fluorotryptamine;
N-Cyclobutylmethyloxycarbonyl-5-fluorotryptamine;
N-(Benzenesulfonyl)tryptamine;
N-(1-(R)-Methoxy-1-phenylacetyl)tryptamine;
N-(1-(S)-Methoxy-1-phenylacetyl)tryptamine;
N-Cyclopropylmethyloxycarbonyltryptamine;
2-Bromo-N-cyclopropylmethyloxycarbonyltryptamine;
2-Bromo-5-fluoro-N-benzyloxycarbonyltryptamine;
2-benzyltryptamine;
N-[(S)-mandeloyl]tryptamine;
N-[(R)-mandeloyl]tryptamine;
2-benzyl-5-methoxytryptamine;
1-[5-Fluoro-3-(2′-ethyl)indolyl]-3-benzylurea;
Di-[N-(methyleneoxycarbonyl)-tryptamine]-1,4-cis-cyclohexane; or
di-[N-(methyleneoxycarbonyl)-tryptamine]-N-octane.

5. A method of treating mammals for sleep disorders which method comprises administering a therapeutically effective amount of a compound of claim 1.

6. A method of treating mammals for sleep disorders which method comprises administering a therapeutically effective amount of a compound of claim 2.

7. A method of treating mammals for sleep disorders which method comprises administering a therapeutically effective amount of a compound of claim 3.

8. A method of treating mammals for sleep disorders which method comprises administering a therapeutically effective amount of a compound of claim 4.

9. A pharmaceutical composition useful for treating sleep disorders which composition comprises a therapeutically effective amount of a compound of claim 1.

10. A pharmaceutical composition useful for treating sleep disorders which composition comprises a therapeutically effective amount of a compound of claim 2.

11. A pharmaceutical composition useful for treating sleep disorders which composition comprises a therapeutically effective amount of a compound of claim 3.

12. A pharmaceutical composition useful for treating system sleep disorders which composition comprises a therapeutically effective amount of a compound of claim 4.

13. A compound of claim 1 which is N-Benzyloxycarbonyl)-5-fluorotryptamine.

14. A method of treating mammals for sleep disorders which method comprises administering a therapeutically effective amount a compound of claim 13.

15. A pharmaceutical composition useful for treating sleep disorders which composition comprises a therapeutically effective amount of a compound of claim 13.

16. A method of treating mammals for sleep disorders which method comprises administering a therapeutically effective amount of a compound of selected from the group consisting of N-(Indole-3-actoyl)D-phenylanine, N-(Indole-3-acetoyl)benzylamine and N-(Indole-3-acetoyl)aniline.

17. A pharmaceutical composition useful for treating sleep disorders which composition comprises a therapeutically selective amount of a compound of selected from the group consisting of N-(Indole-3-acetoyl)D-phenylanine, N-(Indole-3-acetoyl)benzylamine and N-(Indole-3-acetoyl)aniline.

* * * * *